(12) United States Patent
Mori et al.

(10) Patent No.: US 7,432,054 B2
(45) Date of Patent: Oct. 7, 2008

(54) METHOD FOR SEPARATING AND PURIFYING A NUCLEIC ACID

(75) Inventors: Toshihiro Mori, Asaka (JP); Yoshihiko Makino, Asaka (JP)

(73) Assignee: FUJIFILM Corporation, Tokyo (JP)

( * ) Notice: Subject to any disclaimer, the term of this patent is extended or adjusted under 35 U.S.C. 154(b) by 371 days.

(21) Appl. No.: 10/621,715

(22) Filed: Jul. 18, 2003

(65) Prior Publication Data
US 2004/0063122 A1    Apr. 1, 2004

(30) Foreign Application Priority Data
Jul. 19, 2002  (JP) .............................. 2002-210832

(51) Int. Cl.
*C12Q 1/68* (2006.01)
*G01N 33/53* (2006.01)
*G01N 33/567* (2006.01)
*C07H 21/02* (2006.01)

(52) U.S. Cl. .............................. 435/6; 435/7.1; 435/7.2; 536/23.1

(58) Field of Classification Search ....................... None
See application file for complete search history.

(56) References Cited

U.S. PATENT DOCUMENTS

| | | | | |
|---|---|---|---|---|
| 4,090,022 A | * | 5/1978 | Tsao et al. ..................... 536/57 |
| 4,118,336 A | * | 10/1978 | Morishita et al. .............. 502/62 |
| 5,187,083 A | * | 2/1993 | Mullis ........................ 435/91.1 |
| 5,695,946 A | * | 12/1997 | Benjamin et al. .......... 435/7.32 |
| 5,804,684 A | | 9/1998 | Su |
| 6,056,877 A | * | 5/2000 | Gjerde et al. ................ 210/635 |

FOREIGN PATENT DOCUMENTS

| EP | 512767 A1 * | 11/1992 |
|---|---|---|
| EP | 0 580 305 A2 | 1/1994 |
| EP | 1 316 606 A1 | 6/2003 |
| WO | WO 9913976 A1 * | 3/1999 |

OTHER PUBLICATIONS

Yang et al (1998) Proc Nat Acad Sci USA, vol. 95, pp. 5462-5467.*
Van Oss et al (1987) Journal of Chromatography, vol. 391, pp. 53-65.*
GE Osmonics (1997) 'Reducing Background by Filtering Probe and Hybridization Solutions', available online at: http://www.geosmolabstore.com/documents/1237626-Lit-ReducingBackgroundByFilteringProbeAndHybridizationSolutions WithCameoCelluloseAcetate.pdf.*
Whatman (2005) 'Application specific plates', available online at: http://www.whatman.com/products/?pageID=7.30.29.85.*
Corning (2005) available online at: www.corning.com/lifesciences/pdf/lp_filtersystembroch.pdf.*
Pan et al (2003) Nucleic Acids Research, vol. 31, No. 24, pp. 7131-7140.*
Qiagen (1999a) "The world wide standard for ultrapure plasmid DNA", available online at: http://www1.qiagen.com/literature/brochures/plasmid_0499/plasmid_cscl.pdf.*
Qiagen (1999b) "Ultra purity and ultra convenience", available online at: http://www1.qiagen.com/literature/brochures/plasmid_0499/plasmid_silica.pdf.*
Kitos PA et al 'Adsorption of polyadenylate and other polynucleotides to unmodified cellulose.' Biochemistry. Dec. 4, 1973;12(25):5086-91.*
Tomida M et al 'Pregnancy associated increase in mRNA for soluble D-factor/LIF receptor in mouse liver.' FEBS Lett. Nov. 15, 1993;334(2):193-7.*

* cited by examiner

Primary Examiner—Jehanne Sitton
Assistant Examiner—Stephen Kapushoc
(74) Attorney, Agent, or Firm—Birch, Stewart, Kolasch & Birch, LLP (57) ABSTRACT

An object of the present invention is to provide a method for separating and purifying a nucleic acid by adsorbing the nucleic acid in a test sample to a surface of a solid phase and desorbing the nucleic acid by washing and the like. The present invention provides a method for separating and purifying a nucleic acid having a predetermined length from a nucleic acid mixture, comprising a step of: adsorbing and desorbing a nucleic acid in the nucleic acid mixture containing nucleic acids having different lengths to and from a solid phase of an organic macromolecule having a hydroxyl group on surface thereof.

10 Claims, 3 Drawing Sheets

METHOD FOR SEPARATING AND PURIFYING A NUCLEIC ACID

TECHNICAL FIELD

The present invention relates to a method of separating and purifying a nucleic acid. More specifically, the present invention relates to a method of separating and purifying a nucleic acid having a predetermined length from a nucleic acid mixture containing nucleic acids having different lengths.

BACKGROUND ART

The nucleic acid is used in various fields in various forms. For example, in the field of recombinant nucleic acid technology, the nucleic acid is required to be used in the form of a probe, a genomic nucleic acid, and a plasmid nucleic acid.

In diagnostic field, the nucleic acid is also used in various methods. For example, a nucleic acid probe is normally used in detection and diagnosis of a human pathogen. Similarly, the nucleic acid is used in detection of genetic disorders. The nucleic acid is also used in detection of a food contamination substance. In addition, the nucleic acid is normally used in positioning, identification and isolation of an interesting nucleic acid by various reasons such as preparation of a gene map, cloning and expression of recombinant.

In many cases, the nucleic acid can be obtained in a very small amount, and a complicated and time-consuming operation is required for isolation and purification. This frequently time-consuming and complicated operation is easy to cause a loss of the nucleic acid. In purification of the nucleic acid obtained from serum, urine and bacterial culture, risks such as occurrence of contamination and pseudopositive result are added.

One of well known purification methods is exemplified by purification by adsorption of the nucleic acid to the surface of silicon dioxide, silica polymer or magnesium silicate followed by operations such as washing and desorbing (Japanese Examined Patent Application Publication No. 1995-51065.) This method is excellent in separation performance, however, there are problems that (1) it is difficult to industrially produce the adsorption medium of a comparable performance in a large scale, (2) the handling of the medium is inconvenient, and (3) it is difficult to process the medium in various shapes.

SUMMARY OF THE INVENTION

An object of the present invention is to provide a method for separating and purifying a nucleic acid by adsorbing the nucleic acid in a test sample to a surface of a solid phase and desorbing the nucleic acid by washing and the like. Another object of the present invention is to provide a method for separating and purifying the nucleic acid by using a solid phase which is excellent in separation performance and washing efficiency, can be easily processed, and can be mass-produced for those having substantially the same separation performance. A further object of the present invention is to provide a method for separating and purifying a nucleic acid having a predetermined length from a nucleic acid mixture containing nucleic acids having different lengths.

The present inventors intensively studied to solve the above described objects. As a result, they have found that, in a method for separating and purifying a nucleic acid comprising steps of adsorbing and desorbing the nucleic acid to and from a solid phase, the nucleic acid having a predetermined length can be separated from the nucleic acid mixture containing nucleic acids having different lengths by using an organic macromolecule having a hydroxyl group on surface thereof as the solid phase and also using an unit for separation and purification of nucleic acid which contains the solid phase in a container having two openings. The invention has been completed on the basis of these findings.

According to the present invention, there is provided a method for separating and purifying a nucleic acid having a predetermined length from a nucleic acid mixture, comprising a step of:

adsorbing and desorbing a nucleic acid in the nucleic acid mixture containing nucleic acids having different lengths to and from a solid phase of an organic macromolecule having a hydroxyl group on surface thereof.

Preferably, the organic macromolecule having a hydroxyl group on surface thereof is surface-saponified acetylcellulose. More preferably, the organic macromolecule having a hydroxyl groups on surface thereof is surface-saponified triacetylcellulose.

Preferably, the surface-saponification rate of acetylcellulose is 5% or higher, more preferably 10% or higher.

Preferably, acetylcellulose is a pompous film or a non-porous film.

Preferably, a porous film of a surface-saponified acetylcellulose is used as the solid phase, and a nucleic acid having a predetermined length is separated and purified by selecting a surface-saponification rate of acetylcellulose and a pore size of the porous film.

More preferably, the surface-saponification rate of acetyleellulose is 10 to 100% and the pore size of the porous film is 0.1 μm to 10 μm.

Preferably, acetylcellulose is coated on beads.

Preferably, the nucleic acid in a sample solution containing nucleic acids having different lengths is adsorbed to and desorbed from the solid phase of organic macromolecule having a hydroxyl group on surface thereof.

Preferably, the sample solution is a solution prepared by adding a water-soluble organic solvent to a solution obtained by treating a cell or virus-containing test sample with a nucleic acid-solubilizing reagent.

Preferably, the nucleic acid-solubilizing reagent is a guanidine salt, a surfactant and a proteolytic enzyme.

Preferably, The method according to the present invention comprises steps of:

adsorbing the nucleic acid to the solid phase of the organic macromolecule having a hydroxyl group on surface thereof;

washing the solid phase using a nucleic acid-washing buffer; and desorbing the nucleic acid adsorbed to the solid phase by using a liquid capable of desorbing the nucleic acid adsorbed to the solid phase.

Preferably, the nucleic acid-washing buffer is a solution containing 20 to 100% by weight of methanol, ethanol, isopropanol or n-propanol.

Preferably, the liquid capable of desorbing the nucleic acid adsorbed to the solid phase is a solution having a salt concentration of 0.5 M or lower.

Preferably, adsorption and desorption of the nucleic acid is carried out by using an unit for separation and purification of nucleic acid in which a container having at least two openings contains the solid phase of the organic macromolecule having a hydroxyl group on surface thereof.

More preferably, adsorption and desorption of the nucleic acid is carried out by using an unit for separation and purification of nucleic acid which comprises (a) a solid phase of the organic macromolecule having a hydroxyl group on surface thereof, (b) a container having at least two openings and containing the solid phase, and (c) a pressure difference-generating apparatus connected to one opening of the container.

The method according to the present invention may be carried out by steps of:
(a) preparing a sample solution containing a nucleic acid by using a test sample and inserting one opening of an unit for separation and purification of nucleic acid into said sample solution containing the nucleic acid;
(b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase of the organic macromolecule having a hydroxyl group on surface thereof;
(c) making the inside of the container in a pressurized condition by using the pressure difference-generating apparatus connected to the other opening of the unit for separation and purification of nucleic acid, and discharging the sample solution containing the sucked nucleic acid to an outside of the container;
(d) inserting one opening of the unit for separation and purification of nucleic acid into the nucleic acid-washing buffer;
(e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase of the organic macromolecule having a hydroxyl group on surface thereof;
(f) making the inside of the container in the pressurized condition by using the pressure difference-generating apparatus connected to the other opening of the unit for separation and purification of nucleic acid, and discharging the sucked nucleic acid-washing buffer to the outside of the container;
(g) inserting one opening of the unit for separation and purification of nucleic acid into the liquid capable of desorbing the nucleic acid adsorbed to the solid phase of the organic macromolecule having a hydroxyl group on surface thereof;
(h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule having a hydroxyl group on surface thereof to contact the liquid to the solid phase; and
(i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule having a hydroxyl group on surface thereof to the outside of the container.

Alternatively, the method according to the present invention may be carried out by steps of:
(a) preparing a sample solution containing the nucleic acid using a test sample and injecting said sample solution containing the nucleic acid into one opening of the unit for separation and purification of nucleic acid;
(b) making the inside of the container in the pressurized condition by using the pressure difference-generating apparatus connected to said one opening of the unit for separation and purification of nucleic acid, and discharging the injected sample solution containing the nucleic acid from the other opening to contact the sample solution to the solid phase of the organic macromolecule having a hydroxyl group on surface thereof;
(c) injecting the nucleic acid-washing buffer into said one opening of the unit for separation and purification of nucleic acid;
(d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule having a hydroxyl group on surface thereof;
(e) injecting the liquid capable of desorbing the nucleic acid adsorbed to the solid phase of the organic macromolecule having a hydroxyl group on surface thereof into said one opening of the unit for separation and purification of nucleic acid; and
(f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule having a hydroxyl group on surface thereof and discharge the nucleic acid to the outside of the container.

BRIEF DESCRIPTION OF THE DRAWINGS

In FIG. 2, 1 denotes a container, 10 denotes a main body, 101 denotes an opening, 102 denotes a bottom face, 103 denotes a frame, 104 denotes a wall, 105 denotes a step, 121 denotes a space, 122 denotes a space, 123 denotes a space, 13 denotes a pressing member, 131 denotes a hole, 132 denotes a projection, 20 denotes a lid, 21 denotes an opening, and 30 denotes a solid phase;

DETAILED DESCRIPTION OF THE INVENTION

Embodiments of the present invention will be explained below.

The method for separating and purifying a nucleic acid according to the present invention relates to a method of separating and purifying a nucleic acid having a predetermined length from a nucleic acid mixture containing nucleic acids having different lengths, which is characterized in that the method comprises steps of adsorbing and desorbing the nucleic acid in the nucleic acid mixture which contains nucleic acids having different lengths to and from a solid phase of an organic macromolecule having a hydroxyl group on surface thereof.

The term "nucleic acid" in the invention may be a single strand or double strand, and has no limitation of a molecular weight.

The term "nucleic acid mixture" means a mixture containing a plurality of nucleic acid species having different lengths. The type of length of the nucleic acid in the nucleic acid mixture may not be limited, and may be two or more. The upper limit of the length is not particularly limited. The lengths of individual nucleic acids are also not particularly limited, and nucleic acids having any length ranging from several bp's to several Mbp's can be used. In view of handling, the length of nucleic acids is generally from several bp's to several hundred kbp's.

As the organic macromolecule having a hydroxyl group on surface thereof, surface-saponified acetyl cellulose is preferable. Acetyl cellulose may be any one of monoacetyl cellulose, diacetyl cellulose and triacetyl cellulose. Particularly, triacetyl cellulose is preferable. In the present invention, it is preferable to use surface-saponified acetyl cellulose as the solid phase. The surface saponification means that only surface to which a saponifying agent (e.g., NaOH) contacts, is saponified. In the present invention, it is preferable that a structural body of the solid phase is kept as acetyl cellulose and only the surface of the solid phase is saponified. In this way, an amount of hydroxyl groups (density) on the surface of the solid phase can be controlled according to degree of surface saponification treatment (surface saponification degree).

In order to increase surface area of the organic macromolecule having a hydroxyl group on the surface, it is preferable to form the organic macromolecule having a hydroxyl group on the surface into a membrane. Further, acetyl cellulose may be a porous membrane or a non-porous membrane. However, the porous membrane is more preferable. In the case where the solid phase is a porous membrane, it is preferable that the structural body of the membrane remains as acetyl cellulose and only the surface of the structural body is saponified. In this way, on the basis of the degree of surface saponification treatment (surface saponification degree) x the pore size, spatial amount of hydroxyl groups (density) can be controlled. Meanwhile, the structural body of the membrane is composed of acetyl cellulose and thus, a rigid solid phase can be obtained. Here, that the surface of acetyl cellulose is saponified and hydroxyl groups are introduced to the surface only, means that the structural body is kept as acetyl cellulose and the surface is converted to cellulose. When cellulose is used as a raw material, since cellulose cannot be used in liquid, the porous membrane and a flat membrane can not be manufactured industrially.

For example, the membrane of triacetyl cellulose is marketed as a commercial name TAC base from Fuji Photo Film K.K. As the porous membrane of triacetyl cellulose, there is Microfilter FM500 (Fuji Photo Film K.K.).

In addition, for example, it is also preferable to form the triacetyl cellulose membrane on the surface of polyethylene-made beads followed by surface-saponification to give hydroxyl groups to the surface. In this case, triacetyl cellulose is coated on the beads. Material of the beads may be any material which does not contaminate nucleic acids, and is not limited to polyethylene.

In order to increase efficiency of separation of nucleic acid, it is preferred to increase the number of hydroxyl groups. For example, in the case of acetyl cellulose such as triacetyl cellulose, about 5% or higher of the rate of surface saponification is preferable, and 10% or higher is more preferable.

For the surface saponification of acetyl cellulose, an object to be surface-saponified is dipped in an aqueous solution of sodium hydroxide. In order to change the surface saponification rate, the concentration of sodium hydroxide can be changed. The surface saponification rate is determined by quantifying a remaining acetyl group by NMR.

According to a preferable embodiment of the present invention, a porous membrane of the surface-saponified product of acetyl cellulose is used as the solid phase, and the surface saponification rate of acetyl cellulose and the pore size of the porous membrane are selected to separate and purify the nucleic acid having a predetermined length. The surface saponification rate of acetyl cellulose is preferably 10 to 100%, more preferably 20 to 100%, further preferably 30 to 100%, and particularly preferably 40 to 100%. By preparing a plurality of the porous membrane having a surface saponification rate within these ranges, a nucleic acid can be separated and purified according to the present invention. The pore size of the porous membrane is preferably 0.1 µm to 10 µm, more preferably 0.1 µm to 5 µm, further preferably 0.2 µm to 5 µm, and particularly preferably from 0.2 µm to 3 µm. By preparing a plurality of the porous membrane having a pore size within these ranges, a nucleic acid can be separated and purified according to the present invention.

For example, in the Examples in the present specification where a low molecular weight DNA (1.3 kb) and a high molecular weight DNA (48 kb) were used, both the low molecular weight DNA (79% recovery rate) and the high molecular weight DNA (99% recovery rate) were recovered in high rates by using a triacetyl cellulose porous membrane having 100% of surface-saponification rate and 0.2 µm of pore size. In the case where the triacetyl cellulose porous membrane having 50% of surface-saponification rate and 0.2 µm of pore size was used, the recovery rate of the low molecular weight DNA was very low (recovery rate 6%), and the recovery rate of the high molecular weight DNA was relatively (recovery rate 54%). Moreover, in the case where the triacetyl cellulose porous membrane having 100% of surface-saponification rate and 2.5 µm of pore size was used, the recovery rate of the low molecular weight DNA was relatively low (recovery rate 18%), and the recovery rate of the high molecular weight DNA was considerably high (recovery rate 78%).

Therefore, by collecting an adsorbed DNA by using a triacetyl cellulose porous membrane having 50% of surface-saponification rate and 0.2 µm of pore size, a high molecular weight DNA can be purified. On the other hand, a low molecular weight DNA can be purified by collecting the liquid containing DNA that was not adsorbed to the solid phase by using the triacetyl cellulose porous membrane having 100% of surface-saponification rate and 2.5 µm of pore size, followed by contacting the collected liquid to the triacetyl cellulose porous membrane having 100% of surface-saponification rate and 0.2 µm of pore size.

The examples described above are based on an experimental system using a low molecular weight DNA of 1.3 kb and a high molecular weight DNA of 48 kb. According to the invention, for nucleic acids of various sizes contained in a nucleic acid mixture used as a sample, the nucleic acid having a desired size can be purified from the mixture by measuring the recovery rate of each nucleic acid using the acetyl cellulose porous membrane having various surface-saponification rates and various pore sizes and selecting the surface-saponification rate and the pore size optimal to purification of the nucleic acid of the desired size.

More specifically, the invention provides a method of separating and purifying a relatively long nucleic acid (e.g., 10 kb or longer, or more preferably 30 kb or longer) from the nucleic acid mixture containing nucleic acids having different lengths by using a membrane of a low surface-saponification rate (e.g., 50% or lower of surface-saponification rate). Furthermore, according to the invention, by using a porous membrane having a low surface-saponification rate (e.g., 50% or lower of surface-saponification rate) in combination with a porous membrane having a high surface-saponification rate (e.g., higher than 50% of surface-saponification rate, e.g., 100% of surface-saponification rate), there is provided a method for separating and purifying a relatively short (e.g., shorter than 10 kb, more preferably 2 kb or shorter) nucleic acid from the nucleic acid mixture which contains nucleic acids having different lengths.

In the method for separating and purifying a nucleic acid according to the present invention, adsorption and desorption of the nucleic acid can be preferably conducted by using an unit for separation and purification of nucleic acid in which a container having at least two openings contains the solid phase of the organic macromolecule having a hydroxyl group on the surface.

Further preferably, adsorption and desorption of the nucleic acid can be conducted by using an unit for separation and purification of nucleic acid comprising (a) a solid phase of an organic macromolecule having a hydroxyl group on the surface, (b) a container having at least two openings and containing the solid phase, and (c) a pressure difference-generating apparatus connected to one opening of the container.

In this case, a first embodiment of the method for separating and purifying a nucleic acid according to the invention can comprise the following steps of:

(a) preparing a sample solution containing a nucleic acid by using a test sample and inserting one opening of an unit for separation and purification of nucleic acid into said sample solution containing the nucleic acid;

(b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase of the organic macromolecule having a hydroxyl group on surface thereof;

(c) making the inside of the container in a pressurized condition by using the pressure difference-generating apparatus connected to the other opening of the unit for separation and purification of nucleic acid, and discharging the sample solution containing the sucked nucleic acid to an outside of the container;

(d) inserting one opening of the unit for separation and purification of nucleic acid into the nucleic acid-washing buffer;

(e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase of the organic macromolecule having a hydroxyl group on surface thereof;

(f) making the inside of the container in the pressurized condition by using the pressure difference-generating apparatus connected to the other opening of the unit for separation and purification of nucleic acid, and discharging the sucked nucleic acid-washing buffer to the outside of the container;

(g) inserting one opening of the unit for separation and purification of nucleic acid into the liquid capable of desorbing the nucleic acid adsorbed to the solid phase of the organic macromolecule having a hydroxyl group on surface thereof;

(h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule having a hydroxyl group on surface thereof to contact the liquid to the solid phase; and (i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule having a hydroxyl group on surface thereof to the outside of the container.

A second embodiment of the method for separating and purifying a nucleic acid according to the invention can comprise the following steps of:

(a) preparing a sample solution containing the nucleic acid-using a test sample and injecting said sample solution containing the nucleic acid into one opening of the unit for separation and purification of nucleic acid;

(b) making the inside of the container in the pressurized condition by using the pressure difference-generating apparatus connected to said one opening of the unit for separation and purification of nucleic acid, and discharging the injected sample solution containing the nucleic acid from the other opening to contact the sample solution to the solid phase of the organic macromolecule having a hydroxyl group on surface thereof;

(c) injecting the nucleic acid-washing buffer into said one opening of the unit for separation and purification of nucleic acid;

(d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule having a hydroxyl group on surface thereof;

(e) injecting the liquid capable of desorbing the nucleic acid adsorbed to the solid phase of the organic macromolecule having a hydroxyl group on surface thereof into said one opening of the unit for separation and purification of nucleic acid; and (f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule having a hydroxyl group on surface thereof and discharge the nucleic acid to the outside of the container.

The method for separating and purifying a nucleic acid by using the organic macromolecule having a hydroxyl group on the surface, will be described in detail below. Preferably in the present invention, the nucleic acid in the sample solution is adsorbed to the solid phase by contacting the sample solution containing the nucleic acid to the solid phase of the organic macromolecule having a hydroxyl group on surface thereof, and then the nucleic acid adsorbed to the solid phase is desorbed from the solid phase by using a suitable solution described below. More preferably, the sample solution containing the nucleic acid is a solution which is obtained by adding a water-soluble organic solvent to a solution obtained by treating a cell- or virus-containing test sample with a solution capable of solubilizing a cell membrane and a nuclear membrane to disperse the nucleic acid into the solution.

The sample solution containing the nucleic acid which can be used in the present invention is not limited, but for example, in diagnostic fields, the subject solutions are the body fluid such as whole blood, serum, plasma, urine, stool, sperm and saliva which were collected as a test sample, or solutions prepared from biological materials such as plant (or a portion thereof) and animal (or a portion thereof), or their dissolved matters and homogenates.

First, these test samples are treated with an aqueous solution containing a reagent capably of lysing the cell membrane and solubilizing the nucleic acid. By this treatment, the cell membrane and the nuclear membrane are lysed, and the nucleic acid is dispersed into the aqueous solution.

For lysing the cell membrane and solubilizing the nucleic acid, for example, when the subject sample is whole blood, necessary steps are (1) removing erythrocytes, (2) removing various proteins, and (3) lysing leukocytes and lysing the nuclear membrane. (1) Removing erythrocytes and (2) removing various proteins are required to prevent non-specific adsorption to the solid phase and clogging of the porous membrane, and (3) lysing leukocytes and lysing the nuclear membrane is required to solubilize the nucleic acid which is an object of extraction. Particularly, (3) lysing leukocytes and lysing the nuclear membrane is an important step. In the method of the present invention, it is necessary to solubilize the nucleic acid in this step. For example, by incubating the sample for 10 minutes at 60° C. under the condition in which guanidine hydrochloride, Triton X100, and protease K (Sigma made) are added, the above-mentioned (1), (2) and (3) can be achieved simultaneously.

The reagent for solubilizing the nucleic acid which is used in the present invention is exemplified by the solution containing the guanidine salt, a surfactant and a protease.

The guanidine salt is preferably guanidine hydrochloride, but other guanidine salts (guanidine isothiocyanate and guanidine thiocyanate) can also be used. The concentration of guanidine salts in the solution is 0.5 M to 6 M, preferably 1 M to 5 M.

As the surfactant, Triton X100 can be used. Alternatively, an anionic surfactant such as SDS, sodium cholate and sodium sarcosinate, a nonionic surfactant such as Tween 20 and Megafac, and other various types of amphoteric surfactants, can also be used. In the present invention, the nonionic surfactant such as polyoxyethylene octylphenyl ether (Triton X100) is preferably used. The concentration of the surfactant in the solution is normally 0.05% by weight to 10% by weight, particularly preferably 0.1% by weight to 5% by weight.

As the protease, Protease K can be used, but other proteases can also give same effect. The protease is an enzyme and thus, incubation is preferable. The protease is preferably used at 37° C. to 70° C., particularly preferably at 50° C. to 65° C.

An aqueous organic solvent is added to the aqueous solution in which the nucleic acid is dispersed, to contact the nucleic acid to the organic macromolecule having a hydroxyl group on the surface. By this operation, the nucleic acid in the sample solution is adsorbed to the organic macromolecule having a hydroxyl group on the surface. In order to adsorb the nucleic acid which was solubilized by the operation as described hereinabove to the solid phase of the organic macromolecule having a hydroxyl group on the surface, it is necessary that an aqueous organic solvent is mixed with the solubilized nucleic acid mixture solution, and a salt is present in the obtained nucleic acid mixture solution.

By breaking a hydrating structure of a water molecule present around the nucleic acid, the nucleic acid is solubilized in an unstable state. It is presumed that when the nucleic acid in such state is contacted to the solid phase of the organic macromolecule having a hydroxyl group on the surface, a polar group on the surface of the nucleic acid interacts to the polar group on the surface of the solid phase and the nucleic acid is adsorbed to the surface of the solid phase. In the method of the present invention, the state of the nucleic acid can become unstable by mixing the aqueous organic solvent with the solubilized nucleic acid mixture solution and by the presence of the salt in the obtained mixture solution of the nucleic acid.

The aqueous organic solvent used her in is exemplified by ethanol, isopropanol or propanol. Among them, ethanol is preferable. The concentration of the aqueous organic solvent is preferably 5% by weight to 90% by weight, and more preferably 20% by weight to 60% by weight. It is particularly preferable to make the concentration of ethanol to be added as high as possible in a degree in which no coagulant occurs.

As the salt present in the obtained mixture solution of the nucleic acid, various chaotropic substances (guanidium salt, sodium iodide, and sodium perchlorate), sodium chloride, potassium chloride, ammonium chloride, sodium bromide, potassium bromide, calcium bromide, ammonium bromide and the like are preferable. Particularly, guanidium salt has both effects of lysis of cell membrane and solubilization of the nucleic acid, and therefore is particularly preferable.

Subsequently, the organic macromolecule having a hydroxyl group on the surface to which the nucleic acid is adsorbed, is contacted to the nucleic acid-washing buffer solution. This buffer solution has a function of washing out impurities in the sample solution which are adsorbed to the organic macromolecule having a hydroxyl group on the surface together with the nucleic acid. Consequently, the solution should have a composition having no ability of desorbing the nucleic acid from the organic macromolecule having a hydroxyl group on the surface and an ability of desorbing the impurities. The nucleic acid-washing buffer solution is an aqueous solution comprising a main agent, a buffer agent and when required, a surfactant. The main agent is exemplified by an about 10 to 100% by weight (preferably about 20 to 100% by weight and more preferably about 40 to 80% by weight) aqueous solution of methanol, ethanol, isopropanol, n-propanol, butanol, acetone and the like. The buffer agent and the surfactant are exemplified by the previously described buffer agents and surfactants. Among them, a solution containing ethanol, Tris and Triton X100 is preferable. The preferable concentrations of Tris and Triton X100 are 10 to 100 mM and 0.1 to 10% by weight, respectively.

Then, to the solution capable of desorbing the nucleic acid adsorbed to the organic macromolecule having a hydroxyl group on the surface thereof, is contacted the washed organic macromolecule having a hydroxyl group on the surface as described above. This solution contains the target nucleic acid and hence, is collected and subjected to amplification of the nucleic acid by following operation, e.g., PCR (polymerase chain reaction). It is preferable that the solution capable of desorbing the nucleic acid has a low salt concentration and particularly preferably, the solution of 0.5 M or lower salt concentration is used. For this solution, purified distilled water, TE buffer and the like can be used.

The unit for separation and purification of nucleic acid which is used in the invention is an unit for separation and purification of nucleic acid wherein the solid phase of the organic macromolecule having a hydroxyl group on the surface is contained in the container having at least two openings.

The material of the container is not particularly limited, so long as the organic macromolecule having a hydroxyl group on the surface is contained therein and at least two openings can be provided. In view of easiness of manufacturing, a plastic is preferable. For example, clear or opaque resins such as polystyrene, polymethacrylate ester, polyethylene, polypropylene, polyester, nylon, or polycarbonate are preferably used.

Figure 1:
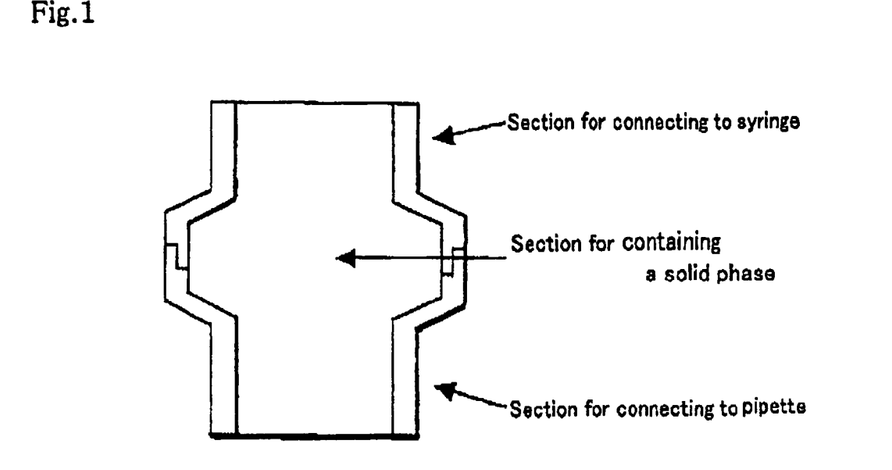
FIG. 1 shows a conceptual diagram of a unit for separation and purification of nucleic acid according to the present invention.

FIG. 1 shows a conceptual diagram of the container. Basically, the container has a section for containing the solid phase, and the solid phase is contained said containing section. The solid phase does not move out of the containing section at the time of sucking and discharging the sample solution and the like. A pressure difference-generating apparatus, e.g., a syringe, is connected to the opening. For this purpose, it is preferable that the container is initially divided into two sections, and after the solid phase is contained, these portions are integrated. In addition, in order to prevent that the solid phase moves out of the containing section, a mesh made of the material which does not contaminat DNA, can be placed on the top and the bottom of the solid phase.

There is no limitation on the shape of the organic macromolecule having a hydroxyl group on the surface which is contained in the container as described above. The shape may be any shape such as discoid, squared, rectangular or ellipsoid; and in the membrane, cylindrical, roll, or beads coated with the organic macromolecule having a hydroxyl group on the surface. In view of manufacturing suitability, the shape having symmetric property such as discoid, squared, cylindrical and roll, and beads are preferable.

The one opening of the container described above is inserted into the sample solution containing the nucleic acid, and the sample solution is contacted to the organic macromolecule having a hydroxyl group on the surface by sucking from the other opening. The sample solution is discharged, and then the nucleic acid-washing buffer solution is sucked and discharged. Then, the solution capable of desorbing the nucleic acid adsorbed to the organic macromolecule having a hydroxyl group on the surface is sucked and discharged. This discharged solution is collected to obtain the target nucleic acid.

Alternatively, by dipping the organic macromolecule having a hydroxyl group on the surface in the sample solution containing the nucleic acid, the nucleic acid-washing buffer solution, and the solution capable of desorbing the nucleic acid adsorbed to the organic macromolecule having a hydroxyl group on the surface, in this order, the target nucleic acid can be obtained.

The unit for separation and purification of nucleic acid used in the invention preferably comprises (a) a solid phase of the organic macromolecule having a hydroxyl group on surface thereof, (b) a container containing the solid phase and having at least two openings, and (c) a pressure difference-generating apparatus connected to one opening of the container. The unit for separation and purification of nucleic acid will be described below.

The container is normally made in a divided form of a main body which contains the solid phase of the organic macromolecule having a hydroxyl group on the surface, and a lid, wherein each has at least one opening. The one is used as an inlet and an outlet of the sample solution containing the nucleic acid, the nucleic acid-washing buffer solution, a liquid capable of desorbing the nucleic acid adsorbed to the solid phase (hereinafter referred to as "sample solution and the like"); and the other is connected to the pressure difference-generating apparatus capable of making the inside of the container in a reduced pressure or pressurized state. There is no limitation of the shape of the main body. In order to make manufacture easy and also make entire diffusion of the sample solution on the solid phase easy, it is preferable that the section is a circular shape. In order to prevent a cutting wastage of the solid, it is also preferable that the section is a squared shape.

It is necessary to connect the lid to the main body so as to make the inside of the container in the reduced pressure state or the pressurized state by using the pressure difference-generating apparatus. If this state is accomplished, the method of connection can be selected freely. For example, use of an adhesive, screwing, fitting, securing, and fusing by ultrasonic heating, are exemplified.

An internal volume of the container is determined only by an amount of the sample solution to be treated. Normally, it is expressed by the volume of the solid phase to be contained. It is preferable to use a size suitable for containing 1 to 6 sheets of the solid phase having about 1 mm or smaller (e.g., around 50 to 500 μm) thickness and about 2 mm to 20 mm diameter.

It is preferable to make an end of the solid phase to contact closely to an inner wall face of the container to prevent the sample solution and the like from being passed.

The bottom surface of the solid phase that is located oppositely to the opening used as the inlet of the sample solution and the like, is not closely contacted to the inner wall of the container, and a space is provided. Thereby, a structure suitable for achieving diffusion of the sample solution and the like evenly as possible on the entire surface of the solid phase, can be formed.

It is preferable to provide a member having a hole in generally a center thereof on the solid phase located oppositely to the other opening, i.e., the opening connected to the pressure difference-generating apparatus. This member pushes the solid phase, and has an efficient effect of discharging the sample solution and the like. This member has preferably a shape having a slope such as a funnel or a cup in such a way that the liquid is collected in the center hole. The size of this hole, an angle of the slope, and the thickness of the member can be properly determined by those skilled in the art in consideration of the amount of the sample solution and the like to be treated and the size of the container for containing the solid phase. Between this member and the opening, a space is preferably provided to store the overflowed sample solution and the like and prevent the sample solution from being sucked into the pressure difference-generating apparatus. The volume of this hole can be properly chosen by those skilled in the art. In order to collect efficiently the nucleic acid, it is preferable to suck the sample solution containing the nucleic acid in an amount which is sufficient for dipping a whole of the solid phase.

In order to prevent the sample solution and the like from being concentrated only beneath the opening through which sucking is carried out and to allow the sample solution and the like to be passed through the solid phase, a space is preferably provided between the solid phase and this member. For this purpose, it is preferable to provide a plurality of projection from the member to the solid phase. The size and number of the projection can be properly chosen by those skilled in the art. It is preferable to make an opening area of the solid phase as large as possible while keeping the space.

When the container has 3 or more openings, in order to make possible sucking and discharging the liquid by pressure-reducing and pressuring operations, it is needless to say that an excess opening should be closed temporarily.

The pressure difference-generating apparatus reduces at first the pressure of the inside of the container which contains the solid phase, so as to suck the sample solution containing the nucleic acid. The pressure difference-generating apparatus is exemplified by the syringe, pipetter, or a pump capable of sucking and pressurizing such as a peristaltic pump. Among them, the syringe is suitable for manual operation and the pump is suitable for automatic operation. The pipetter has an advantage of one hand operation. Preferably, the pressure difference-generating apparatus is releasably connected to the one opening of the container.

Next, the purification method of the nucleic acid using the unit for separation and purification of nucleic acid as described above, will be described. First of all, in the sample solution containing the nucleic acid is inserted one opening of the unit for separation and purification of nucleic acid as described above. Then, by using the pressure difference-generating apparatus connected to the other opening, the pressure of the inside of the purifying unit is reduced to suck the sample solution into the container. By this operation, the sample solution is contacted to the solid phase so as to adsorb the nucleic acid present in the sample solution to the solid phase. At this time, it is preferable to suck the sample solution in such an amount that the solution can be contacted to almost whole of the solid phase. However, sucking of the solution in the pressure difference-generating apparatus causes contamination of the apparatus and hence, the amount is appropriately adjusted.

After an appropriate amount of the sample solution is sucked, the inside of the container of the unit is pressurized by using the pressure difference-generating apparatus, and the sucked liquid is discharged. No interval is required for this operation, and discharge may be carried out immediately after sucking.

Subsequently, the nucleic acid-washing buffer solution is sucked into the container and discharged from it by pressure-reducing and pressurizing operations as described above to wash the inside of the container. This solution has functions of washing out the sample solution left in the container and also washing out impurities in the sample solution adsorbed to the solid phase together with the nucleic acid. Therefore, the solution must have a composition having functions of desorbing no nucleic acid but impurities from the solid phase. The nucleic acid-washing buffer solution is an aqueous solution containing a main agent, a buffer agent and when required, a surfactant. The main agent is exemplified by about 10 to 90% (preferably about 50 to 90%) aqueous solution of methyl alcohol, ethyl alcohol, butyl alcohol, acetone and the like; and the buffer agent and the surfactant are exemplified by the previously described buffer agents and surfactants. Among them, a solution containing ethyl alcohol, Tris and Triton X100 is preferable. The preferable concentrations of Tris and Triton X100 are 10 to 100 mM and 0.1 to 10%, respectively.

Next, a solution capable of desorbing the nucleic acid adsorbed to the solid phase is introduced into the inside of the container and discharged from the container by pressure-reducing and pressurizing operations as described above. This discharged solution contains the target nucleic acid and hence, the target nucleic acid can be collected to be subjected to amplification of the nucleic acid by a following operation, e.g., PCR (polymerase chain reaction).

Figure 2:
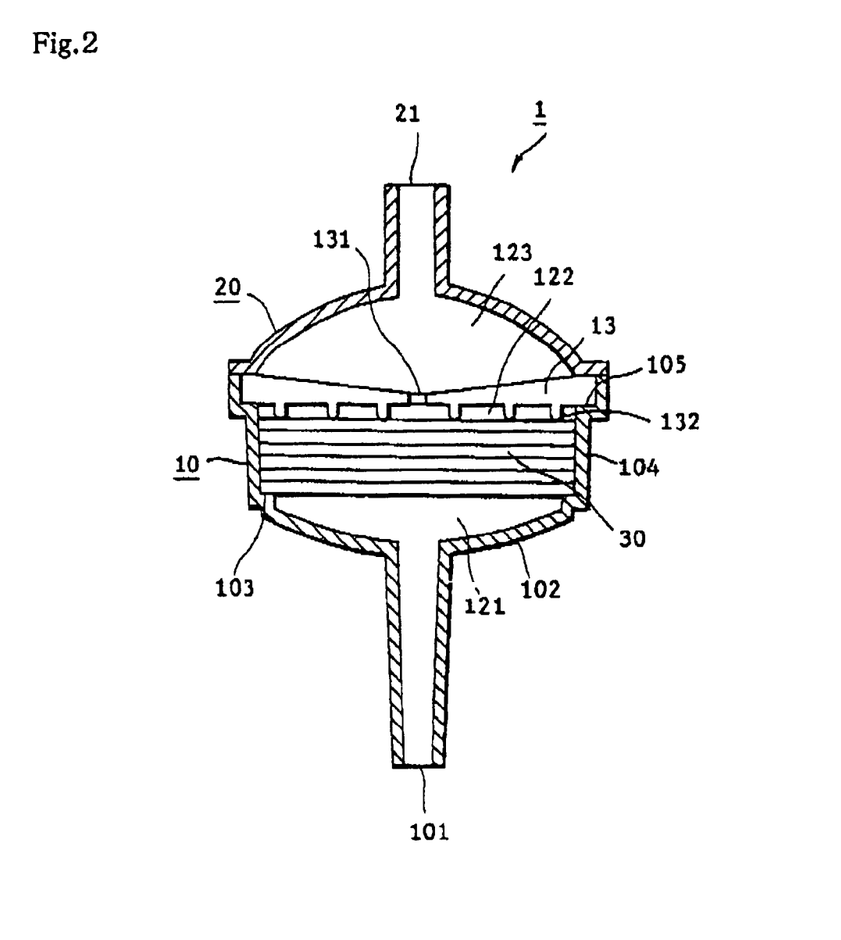
FIG. 2 is an example of the unit for separation and purification of nucleic acid according to the present invention, wherein the pressure difference-generating apparatus to be connected to the opening 21 is not illustrated.

FIG. 2 is a sectional view of an example of the unit for separation and purification of nucleic acid according to the present invention, provided that no pressure difference-generating apparatus is illustrated. A container 1 containing the solid phase comprises a main body 10 and a lid 20 and is made of clear polystyrene. The main body 10 contains saponified triacetyl cellulose membrane as a solid phase 30. In addition, it has an opening 101 for sucking the sample solution and the like. A bottom face 102 extending from the opening is formed in a funnel shape, and a space 121 is formed between this and the solid phase 30. In order to support the solid phase 30 and hold the space 121, a frame 103 which is formed with the bottom face 102, is provided.

The main body has an inner diameter of 20.1 mm, a depth of 5.9 mm, and a length from the bottom face 102 to the opening 101 of about 70 mm. The solid phase 30 which is contained has a diameter of 20.0 mm. The thickness of one sheet of the solid phase is about 50 to 500 μm, and an example of the thickness is 100 μm.

In FIG. 2, a funnel-shaped pressing member 13 is provided on the top of the solid phase. A hole 131 is made in a center of the pressing member 13, and a group of projections 132 are provided downward, and a space 122 is formed between this and the solid phase 30. To prevent leaking of the sample solution and the like from a space between the solid phase 30 and a wall 104 of the main body 10, the inner diameter of the upper portion of the wall 104 is larger than the diameter of the solid phase. The periphery of the pressing member 13 is mounted on a step 105.

A lid 20 is connected to the main body 10 by ultrasonic heating. In almost central part of the lid 20 is provided an opening 21 for connecting the pressure difference-generating apparatus. Between the lid 20 and the pressing member 13 is provided a space 123 for holding the sample solution and the like which flow out from the hole 131. A volume of the space 123 is about 0.1 mL.

The present invention will be described in more detail with reference to examples. However, the present invention is not limited to these examples.

EXAMPLES

Example 1

(1) Preparation of Cartridge for Purification of Nucleic Acid

Figure 3:
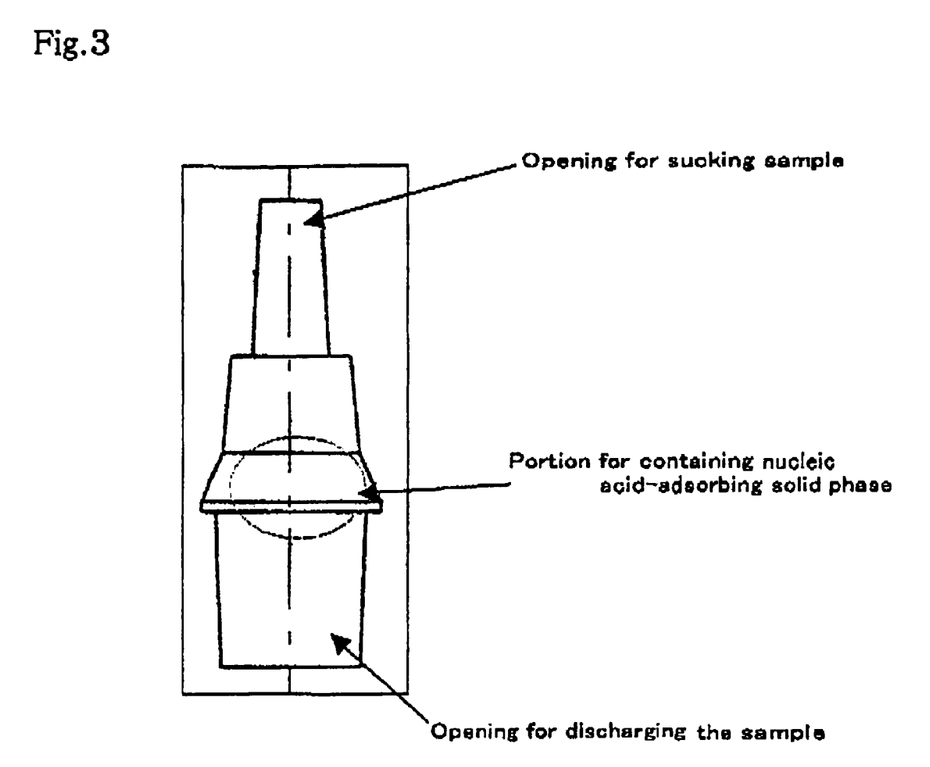
FIG. 3 is a schematic diagram of a cartridge for purification of nucleic acid used in the Example.

A cartridge for purification of nucleic acid having a portion which has 7 mm inner diameter and 2 mm thickness for containing a solid phase for adsorption of a nucleic acid, was prepared by high impact polystyrene. FIG. 3 shows a structure of the prepared cartridge for purification of nucleic acid.

This cartridge for purification of nucleic acid has an opening for sucking a sample, a portion for containing a nucleic acid-adsorbing solid phase, and an opening for discharging the sample. A suction pump is connected to the opening for discharging the sample to suck the sample.

(2) Preparation of Solid Phase for Purification of Nucleic Acid

Solid phases for purification of nucleic acid as shown in Table 1 were prepared. For saponification, treatment was conducted by dipping triacetyl cellulose porous membranes (Fuji Photo Film K.K.) having various pore sizes in 0.1 N sodium hydroxide aqueous solution for 30 minutes in the case of 50% surface saponification, and in 2 N sodium hydroxide aqueous solution for 1 hour in the case of 100% surface saponification. Each of the thus treated solid phases was contained in the portion for containing a nucleic acid-adsorbing solid phase, of the cartridge for purification of nucleic acid which was prepared in the above (1).

TABLE 1

| No. | Pore size (μm) | Surface saponification rate |
|---|---|---|
| 1 | 0.2 | 50% |
| 2 | 0.4 | 50% |
| 3 | 1 | 50% |
| 4 | 2.5 | 50% |
| 5 | 0.2 | 100% |
| 6 | 0.4 | 100% |
| 7 | 1 | 100% |
| 8 | 2.5 | 100% |

(3) Preparation of Adsorption Buffer Solution and Washing Buffer Solution for Purification of Nucleic Acid An adsorption buffer solution and a washing buffer solution for purification of nucleic acid, the compositions of which are shown in Table 2, were prepared.

TABLE 2

| [adsorption buffer] | |
|---|---|
| Guanidine hydrochloride (Life Technology made) | 382 g |
| Tris (Life Technology made) | 12.1 g |
| Triton X100 (ICN made) | 10 g |
| Distilled water | 1000 mL |
| [washing buffer] | |
| 10 mM Tris-HCl 65% ethanol | |

(4) Operation of Nucleic Acid Purification

An aqueous solution containing 1.3 kbp DNA (50 ng/μL) and an aqueous solution containing 48 kbp DNA (50 ng/μL) were prepared. To 200 μL of each of the aqueous DNA solutions were added 200 μL of the adsorption buffer and 200 μL of ethanol, and the mixture was stirred. After stirring, each liquid was sucked and discharged by using cartridges for purification of the nucleic acid having the solid phase for purification of nucleic acid which were prepared in the above (1) and (2).

Moreover, impurities on the cartridge and the adsorbing solid phase were washed out by sucking and discharging 500 μL of the washing buffer.

Finally, 200 μL of distilled water was sucked to collect this liquid.

(5) Quantification of the Amount of Collected Nucleic Acid

Figure 4:
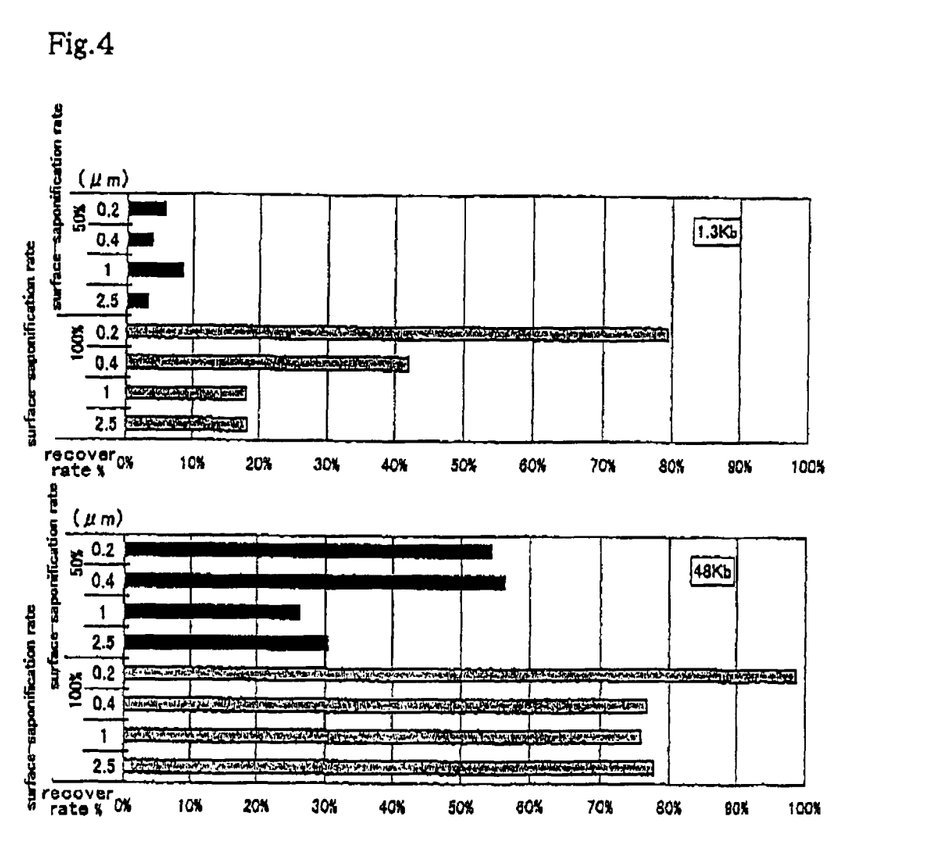
FIG. 4 shows the result of quantification of a collected amount of the nucleic acid which was separated and purified according to the method of the present invention.

By measuring an optical absorption of each of the collected liquid at 260 nm, an amount of the collected DNAs was quantified. The results are shown in Table 3, Table 4 and FIG. 4.

TABLE 3

| | 1.3 kbp DNA (10 μg) | | |
|---|---|---|---|
| Amount of addition | pore size (μm) | collection amount (μg) | collection rate |
| surface-saponification 50% | 0.2 | 0.6 | 6% |
| | 0.4 | 0.4 | 4% |
| | 1 | 0.8 | 8% |
| | 2.5 | 0.3 | 3% |
| surface-saponification 100% | 0.2 | 8.0 | 79% |
| | 0.4 | 4.2 | 42% |
| | 2. | 1.8 | 18% |
| | 2.5 | 1.8 | 18% |

TABLE 4

| | 48 kbp DNA (10 μg) | | |
|---|---|---|---|
| Amount of addition | pore size (μm) | collection amount (μg) | collection rate |
| surface-saponification 50% | 0.2 | 5.4 | 54% |
| | 0.4 | 5.6 | 56% |
| | 1 | 2.6 | 26% |
| | 2.5 | 3.0 | 30% |
| surface-saponification 100% | 0.2 | 9.9 | 99% |
| | 0.4 | 7.7 | 77% |
| | 1 | 7.6 | 76% |
| | 2.5 | 7.8 | 78% |

(6) Purification of low Molecular Weight Nucleic Acid and High Molecular Weight Nucleic Acid From Nucleic Acid Mixture The aqueous solution containing 1.3 kbp DNA and the aqueous solution containing 48 kbp DNA which were used in the above (5), were mixed together to prepare a mixture solution of a low molecular weight nucleic acid and a high molecular weight nucleic acid. By using the obtained mixture, a nucleic acid was purified by the operation which is same as that of the above (4) according to any one method of the following (a) to (c).

(a) Collection with the adsorbing solid phase of 100% surface saponification rate and 0.2 μm pore size.

(b) Collection with the adsorbing solid phase of 50% surface saponification rate and 0.2 μm pore size.

(c) By using the liquid which passed through the adsorbing solid phase of 100% surface saponification rate and 2.5 μm pore size, collection was made with the solid phase same as the above described (a).

Figure 5:
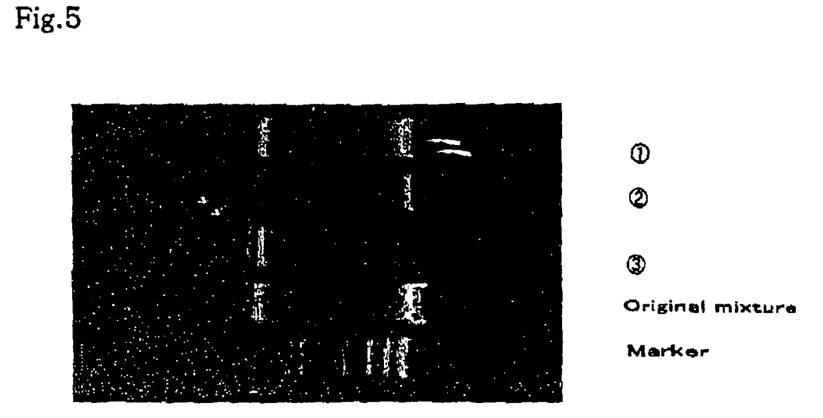
FIG. 5 shows the result of purification of a low molecular weight nucleic acid and a high molecular weight nucleic acid from a nucleic acid mixture according to the method of the present invention. Lanes 1, 2 and 3 correspond to collections (a), (b) and (c) respectively.

The collected liquid of the above (a) to (c) and the mixture solution before purification were subjected to agarose electrophoresis, and photography was carried out. FIG. 5 shows the result. As is clear from the results of FIG. 5, a nucleic acid having a desired size can be purified by selecting the saponification rate and pore size of the solid phase carrier.

INDUSTRIAL APPLICABILITY

By the method for separating and purifying a nucleic acid according to the present invention, which uses a solid phase which is excellent in separation performance, good in washing efficiency, easy in processing, and is capable of mass-production of those having substantially same separation performance, a nucleic acid having a predetermined length can be separated and purified from the nucleic acid mixture containing nucleic acids having different lengths. In addition, operations become easy by using the unit for separation and purification of nucleic acid which was described in the present specification.

What is claimed is:

1. A method for separating and purifying nucleic acids having a length of 2 kb or shorter and nucleic acids having a length of 10 kb or longer from a nucleic acid sample solution comprising said nucleic acids, which comprises the following steps performed in the following order:
adsorbing a nucleic acid mixture comprising nucleic acids having lengths of 2 kb or shorter and comprising nucleic acids having lengths of 10 kb or longer to a first solid phase, wherein the first solid phase comprises a porous film of surface-saponified triacetylcellulose having a surface saponification rate of 50% and a pore size between 0.1 µm and 0.2 µm;
collecting nucleic acids which do not adsorb to the first solid phase to obtain a first flow through fraction;
washing the first solid phase using a nucleic acid-washing buffer;
desorbing the nucleic acids adsorbed to the first solid phase by using a liquid capable of desorbing the nucleic acids adsorbed to the solid phase, thereby obtaining purified and separated nucleic acids having a length of 10 kb or longer;
adsorbing the first flow through fraction to a second solid phase, wherein the second solid phase comprise a porous film of surface-saponified triacetylcellulose having a surface saponification rate of 100% and a pore size of between 2.5 µm and 10 µm;
collecting nucleic acids which do not adsorb to the second solid phase to obtain a second flow through fraction;
adsorbing the second flow through fraction to a third solid phase, wherein the third solid phase comprises porous film of surface-saponified triacetylcellulose having a surface saponification rate of 100% and a pore size of between 0.2 µm and 0.4 µm; washing the third solid phase using a nucleic acid-washing buffer; and
desorbing the nucleic acids adsorbed to the third solid phase by using a liquid capable of desorbing the nucleic acid adsorbed to the third solid phase, thereby obtaining purified and separated nucleic acids having a length of 2 kb or shorter.

2. The method according to claim 1, wherein triacetylcellulose is coated on beads.

3. The method according to claim 1, wherein the sample solution is a solution prepared by adding a water-soluble organic solvent to a solution obtained by treating a cell- or virus-containing test sample with a nucleic acid-solubilizing reagent.

4. The method according to claim 3, wherein the nucleic acid-solubilizing reagent is a guanidine salt, a surfactant and a proteolytic enzyme.

5. The method according to claim 1, wherein the nucleic acid-washing buffer is a solution containing 20 to 100% by weight of methanol, ethanol, isopropanol or n-propanol.

6. The method according to claim 1, wherein the liquid capable of desorbing the nucleic acid adsorbed to the solid phase is a solution having a salt concentration of 0.5 M or lower.

7. The method according to claim 1, wherein adsorbing and desorbing of the nucleic acid is carried out by using an unit for separation and purification of nucleic acid in which a container having at least two openings contains the solid phase.

8. The method according to claim 1, wherein adsorption and desorption of the nucleic acid is carried out by using a unit for separation and purification of the nucleic acid which comprises (a) a solid phase of a porous film of a surface-saponified triacetylcellulose, (b) a container having at least two openings and containing the solid phase, and (c) a pressure difference-generating apparatus connected to one opening of the container.

9. The method according to claim 8, comprising steps of:
(a) preparing a sample solution containing a nucleic acid by using a test sample and inserting one opening of an unit for separation and purification of nucleic acid into said sample solution containing the nucleic acid;
(b) sucking the sample solution containing the nucleic acid by making an inside of the container in a reduced pressure condition by using the pressure difference-generating apparatus connected to the other opening of the unit for separation and purification of nucleic acid, and contacting the sample solution to a solid phase;
(c) making the inside of the container in a pressurized condition by using the pressure difference-generating apparatus connected to the other opening of the unit for separation and purification of nucleic acid, and discharging the sample solution containing the sucked nucleic acid to an outside of the container;
(d) inserting one opening of the unit for separation and purification of nucleic acid into the nucleic acid-washing buffer;
(e) sucking the nucleic acid-washing buffer by making the inside of the container in the reduced pressure condition by using the pressure difference-generating apparatus connected to the other opening of the unit for separation and purification of nucleic acid, and contacting the nucleic acid-washing buffer to the solid phase;
(f) making the inside of the container in the pressurized condition by using the pressure difference-generating apparatus connected to the other opening of the unit for separation and purification of nucleic acid, and discharging the sucked nucleic acid-washing buffer to the outside of the container;
(g) inserting one opening of the unit for separation and purification of nucleic acid into the liquid capable of desorbing the nucleic acid adsorbed to the solid phase;
(h) making the inside of the container in the reduced pressure condition by using the pressure difference-generating apparatus connected to the other opening of the unit for separation and purification of nucleic acid, and sucking the liquid capable of desorbing the nucleic acid adsorbed to the solid phase of the organic macromolecule having a hydroxyl group on surface thereof to contact the liquid to the solid phase; and
(i) making the inside of the container in the pressurized condition by using the pressure difference-generating apparatus connected to the other opening of the unit for separation and purification of nucleic acid, and discharging the liquid capable of desorbing the nucleic acid adsorbed to the solid phase of the organic macromolecule having a hydroxyl group on surface thereof to the outside of the container.

10. The method according to claim 8, comprising steps of:
(a) preparing a sample solution containing the nucleic acid using a test sample and injecting said sample solution containing the nucleic acid into one opening of the unit for separation and purification of nucleic acid;
(b) making the inside of the container in the pressurized condition by using the pressure difference-generating apparatus connected to said one=opening of the unit for separation and purification of nucleic acid, and discharging the injected sample solution containing the nucleic acid from the other opening to contact the sample solution to the solid phase of the organic macromolecule having a hydroxyl group on surface thereof;

(c) injecting the nucleic acid-washing buffer into said one opening of the unit for separation and purification of nucleic acid;

(d) making the inside of the container in the pressurized condition by using the pressure difference-generating apparatus connected to said one opening of the unit for separation and purification of nucleic acid, and discharging the injected nucleic acid-washing buffer from said other opening to contact the nucleic acid-washing buffer to the solid phase of the organic macromolecule having a hydroxyl group on surface thereof;

(e) injecting the liquid capable of desorbing the nucleic acid adsorbed to the solid phase of the organic macromolecule having a hydroxyl group on surface thereof into said one opening of the unit for separation and purification of nucleic acid; and (f) making the inside of the container in the pressurized condition by using the pressure difference-generating apparatus connected to said one opening of the unit for separation and purification of nucleic acid, and discharging the liquid capable of desorbing the injected nucleic acid from said other opening, so as to desorb the nucleic acid adsorbed to the solid phase of the organic macromolecule having a hydroxyl group on surface thereof and discharge the nucleic acid to the outside of the container.

* * * * *